(12) United States Patent
Postma et al.

(10) Patent No.: US 7,294,726 B2
(45) Date of Patent: Nov. 13, 2007

(54) PROCESS FOR PREPARING ALKYLENE OXIDE

(75) Inventors: Johannes Folkert Postma, Moerdijk (NL); Alexander Jan Van Der Veen, Amsterdam (NL)

(73) Assignee: Shell Oil Company, Houston, TX (US)

(*) Notice: Subject to any disclaimer, the term of this patent is extended or adjusted under 35 U.S.C. 154(b) by 339 days.

(21) Appl. No.: 10/393,585

(22) Filed: Mar. 21, 2003

(65) Prior Publication Data

US 2003/0191327 A1  Oct. 9, 2003

(30) Foreign Application Priority Data

Apr. 3, 2002  (EP)  ................... 02252411

(51) Int. Cl.
*C07D 301/19*  (2006.01)
(52) U.S. Cl. ................................................. 549/529
(58) Field of Classification Search ................ 549/529
See application file for complete search history.

(56) References Cited

U.S. PATENT DOCUMENTS 4,367,342 A    1/1983  Wulff et al. ................ 549/529
5,103,027 A    4/1992  Shum et al. ................ 549/529
5,849,937 A *  12/1998 Jubin et al. ................ 549/529
6,365,761 B1 * 4/2002  Derks et al. ................ 549/529

FOREIGN PATENT DOCUMENTS

| EP | 0345856 | | 8/1992 |
| JP | 5059030 | | 3/1993 |
| SU | 1097368 | | 7/1982 |
| SU | 1097368 | * | 8/1991 |
| WO | WO 01/05778 | | 1/2001 |
| WO | WO 01/12617 | | 2/2001 |
| WO | WO 01/70712 | | 9/2001 |

OTHER PUBLICATIONS

Derwent article, Derwent Publications Ltd.. London : Database Accesion No. 1992-371302 XP002211095 (Abstract) : Aug. 1991.
International Search Report, dated Aug. 26, 2003.

* cited by examiner

*Primary Examiner*—Bernard Dentz
*Assistant Examiner*—David E Gallis

(57) ABSTRACT

Process for the preparation of alkylene oxide which process comprises contacting organic hydroperoxide and alkene with a heterogeneous epoxidation catalyst and withdrawing a product stream comprising alkylene oxide and an alcohol as reaction products, in which process fresh catalyst is contacted with feed having a higher molar ratio of alkene to organic hydroperoxide than the molar ratio of normal operation.

12 Claims, No Drawings

PROCESS FOR PREPARING ALKYLENE OXIDE

FIELD OF THE INVENTION

The present invention relates to a process for the preparation of alkylene oxide.

BACKGROUND OF THE INVENTION

The epoxidation of alkene into alkylene oxide by reacting the alkene with an organic hydroperoxide is known in the art.

For instance, in the commonly known method for co-producing propylene oxide and styrene starting from ethylbenzene, the aforementioned epoxidation reaction is applied. In general this co-production process involves the steps of (i) reacting ethylbenzene with oxygen or air to form ethylbenzene hydroperoxide, (ii) reacting the ethylbenzene hydroperoxide thus obtained with propane in the presence of an epoxidation catalyst to yield propylene oxide and 1-phenyl-ethanol, and (iii) converting the 1-phenyl-ethanol into styrene by dehydration using a suitable dehydration catalyst.

Another method for producing alkylene oxide is the coproduction of propylene oxide and methyl tert.-butyl ether (MTBE) starting from isobutane and propane. This process is well known in the art and involves similar reaction steps as the styrene/propylene oxide production process described in the previous paragraph. In the epoxidation step tert-butyl hydroperoxide is reacted with propane forming propylene oxide and tert-butanol in the presence of a heterogeneous epoxidation catalyst. Tert-butanol is subsequently etherified with methanol into MTBE, which is used as an additive in motor fuels.

WO 01/70712 describes a method for the manufacture of oxirane compounds from organic peroxide, other than ethylbenzene hydroperoxide, and olefin in the presence of a fixed bed catalyst, characterized in that the conditions (1) to (4) indicated below are satisfied:
(1) the catalyst bed is divided into n-layers and these are used serially (where n is an integer of value 2 or more),
(2) the fresh organic peroxide is divided and supplied at the entry to each catalyst layer,
(3) fresh olefin is supplied at the entry to the first catalyst layer, and
(4) the reaction mixture discharged from the exit of each catalyst layer except the final catalyst layer is supplied respectively to the entry of the next catalyst layer. WO-A-01/70712 does not relate to a special treatment of fresh catalyst.

SUMMARY OF THE INVENTION

In the process according to the present invention, it has been found that a more active epoxidation catalyst can be obtained by subjecting fresh catalyst to a specific treatment.

It has now surprisingly been found that a higher catalyst activity can be obtained if fresh catalyst is contacted with a feed having a high molar ratio of propane to organic hydroperoxide. The higher catalyst activity was observed during the full life-time of the catalyst.

Therefore, the present invention relates to a process for the preparation of alkylene oxide which process comprises contacting organic hydroperoxide and alkene with a heterogeneous epoxidation catalyst and withdrawing a product stream comprising alkylene oxide and an alcohol as reaction products, in which process fresh catalyst is contacted with feed having a higher molar ratio of alkene to organic hydroperoxide than the molar ratio of normal operation.

DETAILED DESCRIPTION OF THE INVENTION

The epoxidation catalyst used may be any heterogeneous catalyst known in the art to be suitable for catalysing the reaction between an alkene and an organic hydroperoxide to obtain the corresponding alkylene oxide and alcohol. Such heterogeneous epoxidation catalysts are known in the art. The catalyst preferably is a heterogeneous catalyst. The catalyst may comprise as the catalytically active metal one or more transition metals, such as vanadium, molybdenum, tungsten, titanium and zirconium. One particularly suitable class of epoxidation catalysts are the titanium-based catalysts. The titanium can be present as the metal per se or in any other form such as titania and titanium containing salts. Furthermore, it has been found particularly advantageous to use catalysts containing titanium on a silicon containing carrier. A suitable silicon containing carrier is silica. Examples of such catalysts are for instance described in U.S. Pat. No. 4,367,342 and EP-A-0,345,856. U.S. Pat. No. 4,367,342 discloses the use of inorganic oxygen compounds of silicon in chemical composition with at least 0.1% by weight of an oxide or hydroxide of titanium, while EP-A-0,345,856 discloses a titania-on-silica heterogeneous catalyst. According to EP-A-0,345,856 this catalyst is obtainable by impregnating a silicon compound with a stream of gaseous titanium tetrachloride followed by calcination and hydrolysis steps and optionally a silylation step.

When these catalysts are used, very good results are achieved by the present process.

Another catalyst which can be used in the process according to the present invention is a titanium-containing silicon oxide catalyst having (1) a mean pore size of at least 10 A, (2) 5 to 200 A pore size fraction constituting at least 90% of total pore volume, (3) specific pore volume of at least 0.2 cm$^3$/g, and (4) which catalyst is obtained by use of a quaternary ainmonium salt template, followed by removal of the template, which template is [NR$^1$R$^2$R$^3$R$^4$]$^+$ (Within this formula, R1 is a linear or branched hydrocarbon group having a carbon number of 2 to 36, and R$^2$ to R$^4$ indicate alkyl groups having carbon numbers of 1 through 6). The catalyst has been described in more detail in WO-A-01/5778.

Fresh catalyst according to the present invention can be catalyst which has been freshly prepared or catalyst which has been regenerated. A regenerated catalyst which can be used as fresh catalyst in the process according to the present invention, is catalyst of which the activity has been restored as described in WO-A-01/12617.

A catalyst is considered to be a fresh catalyst during the first days of operation, more specifically during the first 7 days, most specifically during the first 3 days of operation.

The catalyst is considered to be in normal operation in the time span of from 15% of its life time to 80% of its life time. The life time of the catalyst is considered to be the time between the start of use of the catalyst and the time when the catalyst must be taken out of operation either to be disposed of or to be regenerated.

Suitable organic hydroperoxides for use in the present invention are secondary and tertiary hydroperoxides derived from a $C_4$–$C_{20}$ aliphatic hydrocarbon, a $C_7$–$C_{20}$ aralkyl hydrocarbon or mixtures thereof. Examples of suitable organic hydroperoxides include tert-butyl hydroperoxide, tertiary amyl hydroperoxide, tertiary octyl hydroperoxide, ethylbenzene hydroperoxide, cyclohexyl hydroperoxide, cumene hydroperoxide and diethyl benzyl hydroperoxide. Of these, ethylbenzene hydroperoxide, cumene hydroperoxide and tert-butyl hydroperoxide are most suitably applied.

The alkene used in the present invention can be any organic compound having at least one aliphatic carbon-carbon double bond. Such compound will generally contain from 2 to 25 carbon atoms and preferably from 3 to 12 carbon atoms, such as propane, 1-butene, 2-butene, 1-pentene, 1-octene, 1-dodecene, styrene and methylstyrene. Most preferably, however, propane is used as the alkene, thus producing propylene oxide in accordance with the process of the present invention.

The most suitable molar ratio of alkene to organic hydroperoxide, depends on specific circumstances such as the epoxidation catalyst used, the temperature employed and the specific alkene and organic hydroperoxide present. Usually the molar ratio of alkene to organic hydroperoxide is of from 1 to 10 during normal operation in a feed in which the epoxidation reaction has not yet started. More specifically, the molar ratio will be of from 2 to 6.

In the process according to the present invention, fresh catalyst is contacted with feed having a molar ratio of alkene to organic hydroperoxide which is higher than the molar ratio of the feed fed to the reactor during normal operation. The feed used when fresh catalyst is present, preferably has a molar ratio of alkene to organic hydroperoxide which is at least 1.2 times the molar ratio of normal operation, more preferably at least 1.3, more preferably at least 1.5 times the molar ratio of normal operation, most preferably at least 1.7 times the molar ratio of normal operation.

More specifically, it is generally preferred to contact fresh catalyst with feed having a molar ratio of alkene to organic hydroperoxide of at least 7 while the molar ratio of alkene to organic hydroperoxide will generally preferably be less than 7 during normal operation. More preferably, the fresh catalyst is contacted with feed having a molar ratio of alkene to organic hydroperoxide of at least 8, more preferably at least 8.5.

Epoxidation reactions are generally carried out in multiple reactors. In view of the exothermic character of the reaction, cooling means will generally be present between the reactors.

A suitable method for carrying out the process according to the present invention comprises letting part of the organic hydroperoxide by-pass the one or more reactors containing fresh catalyst. The organic hydroperoxide can subsequently be added to the process downstream of the reactor(s) containing fresh catalyst. Fresh catalyst in reactors further downstream in a series of reactors will generally not require a special treatment. The ratio of alkene to organic hydroperoxide in these downstream reactors will be high during normal operation as a substantial amount of the organic hydroperoxide in the feed to these reactors already will have reacted.) This leads to a high ratio of alkene to organic hydroperoxide both when fresh catalyst is present and during normal operation.

It is preferred that fresh catalyst in the first part of the epoxidation process is treated according to the present invention if multiple epoxidation reactors are present. The first part is considered to be the first 50% wt of catalyst used for converting organic hydroperoxide with alkene to obtain alkylene oxide and alcohol. More specifically, the first part is considered to be the first 40% wt of catalyst used for converting organic hydroperoxide with alkene to obtain alkylene oxide and alcohol.

If the process is carried out in a single reactor containing at least 2 catalyst beds, it is preferred that at least the first catalyst beds are treated according to the present invention. In this connection, the first catalyst bed(s) are considered to be the catalyst bed(s) containing the first 50% wt of catalyst used for converting organic hydroperoxide with alkene to obtain alkylene oxide and alcohol, more specifically the first 40% wt.

If multiple reactors are used, the process of the present invention preferably is applied to upstream reactors. The expression "upstream" is used to indicate that these reactors are at the beginning of the flow of the feed. In these reactors, the ratio of alkene to organic hydroperoxide will be lower during normal operation than in reactors further downstream which reactors are nearer the end of the flow of feed. In such downstream reactors a substantial amount of hydroperoxide has already been converted.

In commercial operation the average temperature in an epoxidation reactor is typically from 50° C. to 150° C., preferably from 60° C. to 135° C. The pressure in each reactor can be up to 80 bar, preferably from 10 bar to 60 bar. Generally, the reaction medium is in the liquid phase.

It is preferred to use the process according to the present invention in a series of reactors which is operated cyclically. A preferred series of reactors which can be used is a series of at least two serially connected reactors containing a bed of heterogeneous epoxidation catalyst particles and operated in a cyclic mode, followed by at least one additional epoxidation reactor containing a bed of heterogeneous epoxidation catalyst particles, and continuously withdrawing a product stream from the final epoxidation reactor comprising alkylene oxide and an alcohol as reaction products, from which product stream the alkylene oxide end-product is recovered. A preferred series of cyclically operated reactors has been described in more detail in WO-A01/12617.

Preferably, the feed treated in the series of cyclically operated reactors is subsequently treated in a bank of serially connected reactors, comprising at least 2 serially connected reactors. Preferably, the bank comprises from 3 to 7 reactors. The latter bank of reactors is preferably operated in a fixed order. Therefore, the first reactor will remain the first reactor and the final reactor will remain the final reactor independent from the degree to which the catalyst has been deactivated.

Therefore, the process according to the present invention preferably comprises passing at least part of the feed through a series of reactors which is operated cyclically, before passing the feed obtained through a bank of reactors operated in a fixed order in which process part of the organic hydroperoxide feed by-passes the one or more cyclically operated reactors in which fresh catalyst is present. When the outlet temperature of the reactor(s) containing fresh catalyst has become sufficiently low, the by-pass can be reduced and finally stopped. Usually, care is taken to keep the outlet temperature at less than 150° C., more specifically at less than 135° C.

The composition of the feed to the epoxidation reactor is not critical for the process of the present invention in the sense that it may have any composition which is common in commercial operation. Accordingly, in the case of a styrene/propylene oxide co-production process, the feed to the epoxidation unit comprises at least some ethylbenzene hydroperoxide and normally also a substantial amount of ethylbenzene. Propane is either added to the reactor as a separate feed stream or may be added to the ethylbenzene hydroperoxide-containing feed stream prior to entry into the epoxidation reactor(s). The feed may also contain some methyl phenyl ketone and/or 1-phenyl-ethanol formed in the preceding oxidation section or in a preceding epoxidation reactor or contained in a recycle stream. The exact feed composition depends on whether at least part of the feed has already been contacted with a previous series of epoxidation reactors. A typical feed stream to the epoxidation reactor, which is first in line after the preceding oxidation step including oxidation reactor product work-up steps (like washing and distillation), comprises of from 15 to 25 wt % ethylbenzene hydroperoxide, of from 30 to 50 wt % ethylbenzene, of from 30 to 50 wt % propane, of from 0 to 5 wt % 1-phenyl-ethanol and of from 0 to 5 wt % methyl phenyl ketone, to a total of 100 wt %.

In an methyl tertiary butyl ether (MTBE)/propylene oxide co-production process the feed to the epoxidation reactor comprises at least some tert-butyl hydroperoxide (TBHP) in a tert-butanol solvent. Similar as in the styrene/propylene oxide co-production process, propane is either added to the reactor as a separate feed stream or may be added to the TBHP-containing feed stream prior to entry into the epoxidation reactor.

The process according to the present invention can further comprise recovering the alkylene oxide from the product stream comprising alkylene oxide and an alcohol, preferably with the help of distillation.

The process according to the present invention can further comprise recovering the alcohol from the product stream comprising alkylene oxide and an alcohol and dehydrating the alcohol with the help of a dehydration catalyst to obtain the corresponding alkene.

The process according to the present invention can further comprise recovering the alcohol from the product stream comprising alkylene oxide and an alcohol and reacting the alcohol with methanol to obtain an ether.

The invention is further illustrated by the following examples without limiting the scope of the invention to these particular embodiments.

EXAMPLES

The epoxidation catalyst was a catalyst containing titanium on silica which was prepared as described in the Example according to the teaching of EP-A-345856.

The organic hydroperoxide used contained between 30 and 40% wt of ethylbenzene hydroperoxide in ethylbenzene.

The feed was first treated with the help of a series of 4 reactors which was operated cyclically as described in patent application WO 01/12617. The reactor containing fresh catalyst is taken into operation as the last reactor of the series, and is moved upstream each time another reactor containing fresh catalyst is taken into operation. Subsequently, the feed was sent to a bank of serially connected reactors which were operated in a fixed order.

The final product obtained in the bank of reactors operated in fixed order, contained no substantial amount of ethylbenzene hydroperoxide.

Cooling means were present between each of the reactors (both of the cyclically operated reactors and the reactors operated in fixed order) to adjust the temperature of the reaction fluid, with the exception of between the last and the one-but-last reactor operated in a fixed order between which there is no cooling means.

The reactors contained epoxidation catalyst and were operated liquid full at 50 bara pressure. The temperature of the feed being fed to a cyclically operated reactor differed between 40 and 60° C. when fresh catalyst was present to between 88 and 90° C. when the catalyst was taken out of operation. The outlet temperature differed between 80 and 135° C. and between 90 and 100° C., respectively.

The first order reaction rate constant of the epoxidation ($k_0$, in m$^3$/kmol.s), as determined for the first order conversion of ethylbenzene hydroperoxide in the reactor containing the catalyst, was determined at different points in time.

Example 1

The feed described above was treated in the series of reactors operated cyclically. During the first few days, the feed had a ratio of propane to ethylbenzene hydroperoxide which was 1.8 times the molar ratio of alkene to organic hydroperoxide during normal operation. In the course of 2 weeks, the ratio slowly decreased to the molar ratio of alkene to organic hydroperoxide during normal operation by adding additional ethylbenzene hydroperoxide in ethylbenzene.

After the reactor had arrived in the first position and at 80% of the life time of the catalyst, the ln ($k_0$) of the epoxidation catalyst was 7.4.

Comparative Example 1

The feed described above was treated in the series of reactors operated cyclically as described in Example 1 with the difference that both during the first few days on stream and during normal operation, the feed sent to the series of reactors had a molar ratio of propane to ethylbenzene hydroperoxide as during normal operation. This molar ratio was the same as the molar ratio of normal operation applied in Example 1.

After the reactor had arrived in the first position and when the same amount of time had lapsed as in Example 1, the ln ($k_0$) of the epoxidation catalyst was 6.3.

We claim:

1. Process for the preparation of alkylene oxide which process comprises contacting organic hydroperoxide and alkene with a heterogeneous epoxidation catalyst and withdrawing a product stream comprising alkylene oxide and an alcohol as reaction products, in which process fresh catalyst is contacted with feed having a higher molar ratio of alkene to organic hydroperoxide than the molar ratio of normal operation for a period of time and is subsequently contacted with feed having a molar ratio of alkene to organic hydroperoxide for normal operation.

2. Process according to claim 1, in which process fresh catalyst is contacted with feed having a molar ratio of alkene to organic hydroperoxide which is at least 1.2 times the molar ratio of normal operation.

3. Process according to claim 2, which process is carried out in multiple reactors.

4. Process according to claim 2, in which process part of organic hydroperoxide feed by-passes the one or more reactors containing fresh catalyst.

5. Process according to claim 4, which process comprises passing at least part of the feed through a series of reactors which is operated cyclically, before passing the feed obtained through a bank of reactors operated in a fixed order in which process part of organic hydroperoxide feed by-passes the one or more cyclically operated reactors in which fresh catalyst is present.

6. Process according to claim 5, which process further comprises recovering the alkylene oxide from the product stream comprising alkylene oxide and an alcohol.

7. Process according claim 1, which process further comprises recovering the alcohol from the product stream comprising alkylene oxide and an alcohol and dehydrating the alcohol with the help of a dehydration catalyst to obtain the corresponding alkene.

8. Process according to claim 1, which process further comprises recovering the alcohol from the product stream comprising alkylene oxide and an alcohol and reacting the alcohol with methanol to obtain an ether.

9. The process according to claim 6, which process further comprises recovering the alcohol from the product stream comprising alkylene oxide and an alcohol and dehydrating the alcohol with the help of a dehydration catalyst to obtain the corresponding alkene.

10. The process according to claim 6, which process further comprises recovering the alcohol from the product stream comprising alkylene oxide and an alcohol and reacting the alcohol with methanol to obtain an ether.

11. The process according to claim 1 wherein said period of time comprises up to 7 days.

12. The process of claim 1 wherein said period of time comprises up to 3 days.

* * * * *